United States Patent [19]

Böttcher et al.

[11] Patent Number: 5,532,241
[45] Date of Patent: Jul. 2, 1996

[54] PIPERIDINES AND PIPERAZINES

[75] Inventors: Henning Böttcher, Darmstadt; Christoph Seyfried, Seeheim-Jugenheim; Gerd Bartoszyk; Hartmut Greiner, both of Darmstadt, all of Germany

[73] Assignee: Merck Patent Gesellschaft mit beschrankter Haftung, Darmstadt, Germany

[21] Appl. No.: 314,734

[22] Filed: Sep. 29, 1994

[30] Foreign Application Priority Data

Sep. 30, 1993 [DE] Germany .......................... 43 33 254.4

[51] Int. Cl.$^6$ ..................... A61K 31/495; A61K 31/445; C07D 405/10
[52] U.S. Cl. ..................... 514/254; 544/373; 546/201; 514/323
[58] Field of Search ............... 544/373; 514/254

[56] References Cited

U.S. PATENT DOCUMENTS

| 5,002,948 | 3/1991 | Perregaard et al. | 544/373 |
| 5,242,925 | 9/1993 | Böttcher et al. | 514/254 |
| 5,418,237 | 5/1995 | Böttcher et al. | 514/253 |

FOREIGN PATENT DOCUMENTS

| 0490772 | 6/1992 | European Pat. Off. . |
| 4127849 | 2/1993 | Germany . |
| 94/13659 | 6/1994 | WIPO . |

*Primary Examiner*—Emily Bernhardt
*Attorney, Agent, or Firm*—Millen, White, Zelano & Branigan

[57] ABSTRACT

Piperidine and piperazine derivatives of the formula I

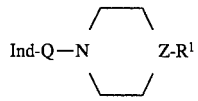

wherein
  Ind is an indol-3-yl radical which is unsubstituted or mono- or polysubstituted by OH, OA, CN, Hal, $COR^2$ or $CH_2R^2$,
  $R^1$ is benzofuran-5-yl or 2,3-dihydrobenzofuran-5-yl, chroman-6-yl, chroman-4-on-6-yl, 3-chromen-6-yl or chromen-4-on-6-yl, which is unsubstituted or monosubstituted by CN, $CH_2OH$, $CH_2OA$ or $COR^2$,
  Q is $C_mH_{2m}$,
  N or $CR^3$,
  A is alkyl having 1–6 C atoms,
  Hal is F, Cl, Br or I,
  $R^2$ is OH, OA, $NH_2$, NHA or $NA_2$,
  $R^3$ is H, OH or OA and
  m is 2, 3 or 4,
and their physiologically acceptable salts, are active on the central nervous system.

17 Claims, No Drawings

PIPERIDINES AND PIPERAZINES

SUMMARY OF THE INVENTION

The invention relates to novel piperidine and piperazine derivatives of the formula I

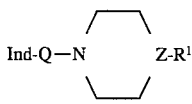

wherein
- Ind is an indol-3-yl radical which is unsubstituted or mono- or polysubstituted by OH, OA, CN, Hal, $COR^2$ or $CH_2R^2$,
- $R^1$ is benzofuran-5-yl or 2,3-dihydrobenzofuran-5-yl, chroman-6-yl, chroman-4-on-6-yl, 3-chromen-6-yl or chromen-4-on-6-yl, which is unsubstituted or monosubstituted by CN, $CH_2OH$, $CH_2OA$ or $COR^2$,
- Q is $C_mH_{2m}$,
- Z is N or $CR^3$,
- A is alkyl having 1–6 C atoms,
- Hal is F, Cl, Br or I,
- $R^2$ is OH, OA, $NH_2$, NHA or $NA_2$,
- $R^3$ is H, OH or OA and
- m 2, 3 or 4, and to their physiologically acceptable salts.

An object of the invention is to provide novel compounds capable of being used for the preparation of drugs.

Upon further study of the specification and appended claims, further objects and advantages of this invention will become apparent to those skilled in the art.

It has been found that the compounds of the formula I and their physiologically acceptable acid addition salts possess valuable pharmacological properties. Thus, in particular, they are active on the central nervous system, especially in terms of $5\text{-HT}_{1A}$-agonist and 5-HT-reuptake inhibition. The compounds are furthermore active as serotonin agonists and antagonists. They inhibit the binding of tritiated serotonin ligands to hippocampal receptors (Cossery et al., European J. Pharmacol., 140:143–155 (1987)). They also modify the accumulation of DOPA in the corpus striatum and the accumulation of 5-HTP in the nuclei raphes (Seyfried et al., European J. Pharmacol., 160:31–41 (1989)). They also have analgesic and hypotensive effects; thus, in catheterized, conscious, spontaneously hypertensive rats (strain: SHR/Okamoto/NIH-MO-CHB-Kisslegg; method: q.v. Weeks and Jones, Proc. Soc. Exptl. Biol. Med., 104:646–648 (1960)), the directly measured blood pressure is lowered after oral administration of the compounds. They are also useful for prophylaxis and control of the sequelae of cerebral infarction (apoplexia cerebri) such as stroke and cerebral ischaemia.

Compounds of the formula I and their physiologically acceptable acid addition salts can, therefore, be used as active ingredients for anxiolytics, antidepressants, antipsychotics, neuroleptics, and/or antihypertensives, and also as intermediates for the preparation of other pharmaceutical active ingredients.

The invention relates to the piperidine and piperazine derivatives of the formula I and to their physiologically acceptable acid addition salts.

The radical A is alkyl having 1, 2, 3, 4, 5 or 6 C atoms, especially 1 or 2 C atoms, preferably methyl and also ethyl, n-propyl, isopropyl, n-butyl, sec-butyl or tert-butyl. OA is preferably methoxy and also ethoxy, n-propoxy, isopropoxy, n-butoxy, isobutoxy, sec-butoxy or tert-butoxy. NHA is preferably methylamino and also ethylamino, isopropylamino, n-butylamino, isobutylamino, sec-butylamino or tert-butylamino. $NA_2$ is preferably dimethylamino and also N-ethyl-N-methylamino, diethylamino, di-n-propylamino, diisopropylamino or di-n-butylamino.

Analogously, CO—NHA is preferably N-methylcarbamoyl or N-ethylcarbamoyl; CO—$NA_2$ is preferably N,N-dimethylcarbamoyl or N,N-diethylcarbamoyl.

The radical Ind is an indol-3-yl radical which is unsubstituted or mono- or, for example, disubstituted by the radicals indicated. Preferably, it is substituted in the 5-position. Substitution in the 4-, 6- or 7-position is also suitable. Furthermore, substitution in the 1- or 2-position is possible. Preferred substituents on the indol-3-yl radical are OH, OA, CN, $CONH_2$, $CH_2OH$, but also $CO_2H$, F, Cl, Br, I, $CH_2NH_2$, CONHA or $CONA_2$, where A preferably corresponds to methyl or ethyl.

The radical $R^1$ is preferably benzofuran-5-yl, 2,3-dihydrobenzofuran-5-yl, chroman-6-yl or chromen-4-on-6-yl, which is unsubstituted or monosubstituted by —$CH_2OH$, —$CONH_2$, —$CO_2A$ or —$CO_2NHA$.

Q is preferably —$(CH_2)_4$—, but also —$(CH_2)_2$— or —$(CH_2)_3$—, while Z is preferably —N—, —C (OH)— or —CH—.

Accordingly, the invention relates particularly to those compounds of the formula I in which at least one of said radicals has one of the meanings indicated above, especially one of the preferred meanings indicated above. Some preferred groups of compounds can be expressed by the following partial formulae Ia to Ig, which correspond to formula I and in which the radicals and parameters not described in greater detail are as defined for formula I, but in which:

- in Ia, Ind is an indol-3-yl radical substituted in the 5-position by OH or OA;
- in Ib, Ind is an indol-3-yl radical substituted in the 5-position by $CONH_2$ or by CN;
- in Ic, Z is N and $R^1$ is substituted or unsubstituted benzofuran-5-yl;
- in Id, Z is —C(OH)— and $R^1$ is substituted or unsubstituted benzofuran-5-yl;
- in Ie, Z is N and $R^1$ is 2,3-dihydrobenzofuran-5-yl;
- in If, Z is N and $R^1$ is chroman-6-yl;
- in Ig, Z is N and $R^1$ is chromen-4-on-6-yl.

Especially preferred compounds are those of partial formulae Ih and Iah to Igh, which correspond to partial formulae I and Ia to Ig, but in which additionally: Q is —$(CH_2)_4$—.

The invention further relates to a process for the preparation of indole derivatives of the formula I and their salts, characterized in that a compound of the formula II

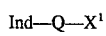

wherein
- $X^1$ is X or $NH_2$,
- X is Cl, Br, I, OH or an OH group functionally modified to form a reactive group, and
- Ind and Q are as defined, is reacted with a compound of the formula III

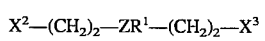

wherein $X^2$ and $X^3$ can be identical or different and are each X if $X^1$=NH$_2$ or are together NH in other cases, and Z and $R^1$ are as defined, or in that to prepare a compound of the formula I in which Z is N, a compound of the formula IV Ind—Q—N(CH$_2$—CH$_2$—X)$_2$  IV wherein X, Q and Ind are as defined, is reacted with a compound of the formula V $R^1$—NH$_2$  V wherein $R^1$ is as defined, or in that a compound which has formula I except that one or more hydrogen atoms have been replaced by one or more reducible groups and/or one or more additional C—C and/or C—N bonds are treated with a reducing agent, or in that a compound which has formula I except that one or more hydrogen atoms have been replaced by one or more solvolyzable groups is treated with a solvolyzing agent, and/or in that an OA group is optionally cleaved to form an OH group, and/or an Ind group and/or an Ar group is converted into another Ind and/or Ar group, and/or in that a resulting base or acid of the formula I is converted into one of its salts by treatment with an acid or base.

The compounds of the formula I are otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York; German Offenlegungsschrift 41 01 686), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compounds of the formula I.

In the compounds of the formula II, $X^1$ is preferably X; accordingly, in the compounds of the formula III, $X^2$ and $X^3$ are together preferably NH. The radical X is preferably Cl or Br, but it can also be I, OH or an OH group functionally modified to form a reactive group, especially alkylsulfonyloxy having 1–6 C atoms (e.g., methanesulfonyloxy) or arylsulfonyloxy having 6–10 C atoms (e.g., benzenesulfonyloxy, p-toluenesulfonyloxy, naphthalene-1- or -2-sulfonyloxy).

Accordingly, the indole derivatives of the formula I can be obtained especially by reacting compounds of the formula Ind—Q—Cl or Ind—Q—Br with piperidine/piperazine derivatives of the formula III in which $X^2$ and $X^3$ together are an NH group (designated as IIIa hereafter).

Some of the compounds of the formulae II and, in particular, III are known; the unknown compounds of the formulae II and III can easily be prepared analogously to the known compounds.

Primary alcohols of the formula Ind—Q—OH can be obtained, e.g., by reducing the appropriate carboxylic acids or their esters. Treatment with thionyl chloride, hydrogen bromide, phosphorus tribromide or similar halogen compounds yields the corresponding halides of the formula Ind—Q—Hal. The corresponding sulfonyloxy compounds can be obtained from the alcohols Ind—Q—OH by reaction with the appropriate sulfonyl chlorides.

The iodine compounds of the formula Ind—Q—I can be obtained, e.g., by reacting potassium iodide with the appropriate p-toluenesulfonic acid esters. The amines of the formula Ind—Q—N$_2$ can be prepared, e.g., from the halides with potassium phthalimide or by reducing the appropriate nitriles.

Most of the piperazine derivatives IIIa are known and can be obtained, e.g., by reacting bis(2-chloroethyl)amine or bis(2-chloroethyl)ammonium chloride with 5-aminobenzofuran, 2,3-dihydro-5-aminobenzofuran, 6-aminochroman or 6-aminochromen-4-one or an appropriately substituted derivative of the compounds mentioned. Compounds of the formula III ($X^2$ and $X^3$=X in each case) can be prepared., e.g., by reducing diesters of the formula alky 1 00C—CH$_2$—ZR$^1$—CH$_2$—COO—alkyl to give compounds of the formula HO—CH$_2$—CH$_2$—ZR$^1$—CH$_2$-CH$_2$OH (III, $X^2$=$X^3$=OH), this being followed, if desired, by reaction with SOCl$_2$ or PBr$_3$.

The reaction of the compounds of formulae II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons such as benzene, toluene or xylene; ketones such as acetone or butanone; alcohols such as methanol, ethanol, isopropanol or n-butanol; ethers such as tetrahydrofuran (THF) or dioxane; amides such as dimethylformamide (DMF) or N-methylpyrrolidone; or nitriles such as acetonitrile, or else, if desired, mixtures of these solvents with one another or mixtures with water. It can be favorable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of the amine component Ind—Q—NH$_2$ or of the piperidine or piperazine derivative of the formula IIIa. The reaction time is between about a few minutes and 14 days, depending on the conditions used, and the reaction temperature is preferably about 0°–150°, normally 20°–130°.

It is also possible to obtain a compound of the formula I by reacting a compound of the formula Ind—Q—N(CH$_2$—CH$_2$—X)$_2$ (IV) with a compound of the formula $R^1$—NH$_2$ (V).

Most of the compounds of the formula V are known; the unknown compounds can easily be prepared analogously to the known compounds. For example, starting from the appropriately substituted nitro compounds, they can be converted into the amines of the formula V by reduction. The compounds of the formula IV can be prepared by reaction of Ind—Q—Cl, Ind—Q—Br or Ind—Q—I with secondary amines of the formula HN(CH$_2$—CH$_2$—X)$_2$.

The reaction of compounds IV and V proceeds according to methods which are known from the literature and were given above for the alkylation of amines.

A compound of the formula I can also be obtained by treating a precursor, in which hydrogen atoms have been replaced by one or more reducible groups and/or one or more additional C—C and/or C—N bonds, with a reducing agent, preferably at temperatures of about −80 to 250°, in the presence of at least one inert solvent.

Reducible groups (groups replaceable by hydrogen) are, in particular, oxygen in a carbonyl group, hydroxyl, arylsulfonyloxy (e.g. p-toluenesulfonyloxy), N-benzenesulfonyl, N-benzyl or O-benzyl.

In principle, compounds containing only one of the above-mentioned groups or additional bonds, or compounds containing two or more of the above-mentioned groups or additional bonds adjacent to one another, can be converted into a compound of the formula I by reduction, it being possible simultaneously to reduce substituents in the Ind group which are present in the starting compound. This is preferably carried out using nascent hydrogen or complex metal hydrides or by means of a Wolff-Kishner reduction or the reductions with hydrogen gas under transition metal catalysis.

Preferred starting materials for the reduction have formula VI

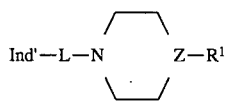   VI wherein

Ind' is an Ind radical which can additionally be substituted in the 1-position by an arylsulfonyl group or an alkyloxycarbonyl group, L is Q or a chain which corresponds to the radical Q except that one or more —$CH_2$— groups have been replaced by —CO— and/or one or more hydrogen atoms have been replaced by one or more OH groups or a double bond, and $R^1$ has the meaning given, but wherein the following meanings cannot apply simultaneously: Ind'=Ind and L=Q.

In the compounds of the formula VI, L is preferably —CO—$(CH_2)_{n-2}$—CO—, wherein n is 2, 3 or 4 [specifically —COCO—, —$COCH_2CO$—, —CO—$(CH_2)_2$—CO—, —CO—$(CH_2)_3$—CO—], —$(CH_2)_{n-1}$—CO—, wherein n is 2, 3 or 4 [specifically —$CH_2$—CO—, —$CH_2CH_2$—CO—, —$(CH_2)_3$—CO— or —$(CH_2)_4$—CO—], further examples being —CO—$CH_2CH_2$—, —CO—$(CH_2)_3$—, —$CH_2$—CO—$CH_2CH_2$— or —$CH_2CH_2$—CO—$CH_2$—.

Compounds of the formula VI can be prepared, e.g., by reacting 4-$R^1$-piperazine or 4-$R^1$-piperidine with a compound of the formula VII Ind'—L—$X^1$     VII wherein $R^1$ Ind', L and $X^1$ are as defined above, under the conditions indicated above for the reaction of II with III.

If nascent hydrogen is used as the reducing agent, this can be produced, e.g., by treating metals with weak acids or with bases. Thus, it is possible, e.g., to use a mixture of zinc with an alkali metal hydroxide solution or a mixture of iron with acetic acid. It is also appropriate to use sodium or another alkali metal dissolved in an alcohol such as ethanol, isopropanol, butanol, amyl or isoamyl alcohol or phenol. It is also possible to use an aluminum-nickel alloy in aqueous-alkaline solution, ethanol being added if necessary. Sodium amalgam or aluminum amalgam in aqueous-alcoholic or aqueous solution is also suitable for producing the nascent hydrogen. The reaction can also be carried out in the heterogeneous phase, in which case it is convenient to use an aqueous phase and a benzene or toluene phase.

Other reducing agents which can be used to particular advantage are complex metal hydrides such as $LiAlH_4$, $NaBH_4$, diisobutylaluminum hydride or $NaAl(OCH_2CH_2OCH_3)_2H_2$, and diborane, catalysts such as $BF_3$, $AlCl_3$ or LiBr being added if desired. Solvents which are suitable for this purpose are, in particular, ethers such as diethyl ether, di-n-butyl ether, THF, dioxane, diglyme or 1,2-dimethoxyethane, and hydrocarbons such as benzene. Solvents which are suitable for a reduction with $NaBH_4$ are primarily alcohols such as methanol or ethanol, as well as water and aqueous alcohols. Reduction by these methods is preferably carried out at temperatures of about −80 to +150°, especially about 0°–100°.

The reduction of —CO— groups in acid amides (e.g., those of the formula VI in which L is a —$(CH_2)_{n-1}$—CO— group) to $CH_2$ groups can be carried out to particular advantage with $LiAlH_4$ in THF at temperatures of preferably about 0°–66°. Arylsulfonyl protecting groups located in the 1-position of the indole ring can be simultaneously eliminated by reduction. N-Benzyl groups can be eliminated by reduction with sodium in liquid ammonia.

It is also possible to reduce one or more carbonyl groups to $CH_2$ groups according to the Wolff-Kishner method, e.g., by treatment with anhydrous hydrazine in absolute ethanol, under pressure, at temperatures of preferably about 150°–250°. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 3–4 hours. The water is then distilled off and the hydrazone formed is decomposed at temperatures of up to about 200°. The Wolff-Kishner reduction can also be carried out with hydrazine in dimethyl sulfoxide at room temperature.

Moreover, it is possible to carry out certain reductions by using $H_2$ gas under the catalytic action of transition metals, such as, e.g., Raney Ni or Pd. In this way, e.g., Cl, Br, I, SH or, in certain cases, even OH groups can be replaced by hydrogen. Nitro groups can also be converted into $NH_2$ groups by catalytic hydrogenation with $Pd/H_2$ in methanol.

Compounds which have formula I except that one or more H atoms have been replaced by one or more solvolyzable groups can be solvolyzed, especially hydrolyzed, to give the compounds of the formula I.

The starting materials for the solvolysis can be obtained for example by reacting IIIa with compounds which have formula II ($X^1$=X) except that one or more H atoms have been replaced by one or more solvolyzable groups. Thus, in particular, 1-acylindole derivatives (which have formula I except that, in the 1-position of the Ind radical, they contain an acyl group, preferably an alkoxycarbonyl, alkanoyl, alkylsulfonyl or arylsulfonyl group having up to 10 C atoms in each case, such as methanesulfonyl, benzenesulfonyl or p-toluenesulfonyl) can be hydrolyzed to give the corresponding indole derivatives unsubstituted in the 1-position of the indole ring, e.g. in an acidic or, preferably, neutral or alkaline medium at temperatures of preferably about 0°–200°. Sodium, potassium or calcium hydroxide, sodium or potassium carbonate, or ammonia, is conveniently used as the base. The chosen solvents are preferably water; lower alcohols such as methanol or ethanol; ethers such as THF or dioxane; sulfones such as tetramethylene sulfone; or mixtures thereof, especially mixtures containing water. Hydrolysis can also be carried out simply by treatment with water alone, especially at the boiling point.

A compound of the formula I can furthermore be converted to another compound of the formula I by methods known per se.

Compounds of the formula I in which Ind is an indol-3-yl radical substituted by CO-$R^1$ can be obtained by derivatizing appropriate carboxyindol-3-yl compounds. It is possible, e.g., to esterify the acids with appropriate alcohols or alcoholates, using methods known per se. It is also possible to amidate acids or esters with primary or secondary amines. It is preferred to react the free carboxylic acid with the amine under the conditions of a peptide synthesis. This reaction is preferably carried out in the presence of a dehydrating agent, e.g., a carbodiimide such as dicyclohexylcarbodiimide or else N-(3-dimethylaminopropyl)-N-ethylcarbodiimide, or propanephosphonic anhydride (q.v. Angew. Chem. 92, 129 (1980)), diphenylphosphoryl azide or 2-ethoxy-N-ethoxycarbonyl-1,2-dihydroquinoline, in an inert solvent, e.g., a halogenated hydrocarbon such as methylene chloride, an ether such as THF or dioxane, an amide such as DMF or dimethylacetamide, or a nitrile such as acetonitrile, at temperatures of preferably about −10 to 40, preferably about 0°–30°. Instead of the acid or amide, it is also possible to use reactive derivatives of these substances in the reaction, e.g., those in which reactive groups are blocked by protecting groups in an intermediate step. The acids can also be used in the form of their activated esters, which are conveniently formed in situ, e.g., by the addition of 1-hydroxybenztriazole or N-hydroxysuccinimide.

Furthermore, cyano-substituted indol-3-yl radicals can be hydrolyzed to give carboxy-indol-3-yl or carbamido-indol-3-yl radicals.

Conversely, however, it is particularly convenient to prepare the nitriles by elimination of water, starting from the amides, e.g., by means of trichloroacetyl chloride/Et$_3$N [Synthesis (2), 184, (1985)] or with POCl$_3$ (J. Org. Chem. 26, 1003 (1961)).

A base of the formula I can be converted with an acid into the corresponding acid addition salt. Acids which produce physiologically acceptable salts are suitable for this reaction. Thus, it is possible to use inorganic acids, e.g., sulfuric acid, hydrohalic acids such as hydrochloric acid or hydrobromic acid, phosphoric acids such as orthophosphoric acid, nitric acid and sulfamic acid, as well as organic acids, i.e., specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid.

If desired, the free bases of the formula I can be liberated from their salts by treatment with strong bases such as sodium or potassium hydroxide or sodium or potassium carbonate provided there are no other acid groups in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of the formula I and their physiologically acceptable salts for the manufacture of pharmaceutical preparations, especially by a non-chemical route. For this purpose, they can be converted into a suitable dosage form together with at least one excipient or adjunct and, if appropriate, in combination with one or more additional active ingredients.

The invention further relates to compositions, especially pharmaceutical preparations, containing at least one compound of the formula I and/or one of their physiologically acceptable salts. These preparations can be used as drugs in human or veterinary medicine. Possible excipients are organic or inorganic substances which are suitable for enteral (e.g.,oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used, e.g., to manufacture injectable preparations.

The preparations indicated can be sterilized and/or can contain adjuncts such as lubricants, preservatives, stabilizers and/or wetting agents, emulsifiers, salts for influencing the osmotic pressure, buffer substances, colorants, taste correctors and/or flavorings. If desired, they can also contain one or more additional active ingredients, e.g. one or more vitamins.

The compounds of the formula I and their physiologically acceptable salts can be used for the therapeutic treatment of the human or animal body and for controlling diseases. They can be used for treating disorders of the central nervous system, such as tension, depressions and/or psychoses, and side-effects in the treatment of hypertension (e.g., with α-methyldopa). The compounds can also be used in endocrinology and gynecology, e.g., for the therapeutic treatment of acromegaly, hypogonadism, secondary amenorrhea, premenstrual syndrome and undesired puerperal lactation, and also for the prophylaxis and therapy of cerebral disorders (e.g., migraine), especially in geriatrics in a manner similar to certain ergot alkaloids and for controlling the sequelae of cerebral infarction (apoplexia cerebri), such as stroke and cerebral ischemia.

In these treatments, the substances of the invention are normally administered analogously to known, commercially available preparations (e.g., bromocriptine, dihydroergocornine), preferably in dosages of about 0.2–500 mg, especially 0.2–50 mg per dosage unit. The daily dosage is preferably about 0.001–10 mg/kg of body weight. The low dosages (about 0.2–1 mg per dosage unit; about 0.001–0.005 mg/kg of body weight) are particularly suitable for use as antimigraine preparations; dosages of about 10–50 mg per dosage unit are preferred for the other indications. However, the particular dose for each individual patient depends on a very wide variety of factors, for example, the activity of the particular compound used, age, body weight, general state of health, sex, diet, time and method of administration, rate of excretion, drug combination and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 33 254.4, filed Sep. 30, 1993, are hereby incorporated by reference.

In the following Examples, "working-up in conventional manner" means: Water is added if necessary, extraction is carried out with methylene chloride, the organic phase is separated off, dried over sodium sulfate and filtered, the filtrate is evaporated and the residue is purified by chromatography on silica gel and/or by crystallization. Temperatures are given in ° C. Rf values were obtained by thin layer chromatography on silica gel.

EXAMPLES

Example 1

1.8 g of 3-(4-chlorobutyl)-5-methoxyindole [obtainable by diazotization of p-methoxyaniline, reaction with ethyl cyclohexanone-2-carboxylate according to Japp-Klingemann to give 4-(2-carbethoxyindol-3-yl)butyric acid, alkaline hydrolysis, decarboxylation, reduction with LiAlH$_4$ and reaction with SOCl$_2$] and 1.9 g of 1-(2-hydroxymethylbenzofuran-5-yl)piperazine [obtainable by reaction of N,N-bis(2-chloroethyl)amine with 2-hydroxymethyl-5-aminobenzofuran] are dissolved in 200 ml of acetonitrile and the mixture is stirred at room temperature for 10 hours. Customary working up gives 1-[4-(5-methoxyindol-3-yl)butyl]-4-(2-hydroxymethylbenzofuran- 5-yl)piperazine, m.p. 159°.

The following are obtained analogously by reaction of 3-(4-chlorobutyl)-5-methoxyindole with 1-(2,3-dihydrobenzofuran- 5-yl)piperazine:

1-[4-(5-methoxyindol-3-yl)butyl]-4-(2,3-dihydrobenzofuran- 5-yl)piperazine, m.p. 111°–112°;

of 3-(4-chlorobutyl)-5-hydroxyindole with 1-(chroman-6-yl)piperazine:

1-[4-(5-hydroxyindol-3-yl)butyl]-4-(chroman-6-yl)piperazine, m.p. 220°–222°;

of 3-(4-chlorobutyl)-5-methoxyindole with 1-(chroman-6-yl)piperazine:

1-[4-(5-methoxyindol-3-yl)butyl]-4-(chroman-6-yl)piperazine, m.p. 129°–130°;

of methyl 3-(4-chlorobutyl)-5-indolecarboxylate with 1-(chroman-6-yl)piperazine:

1-[4-(5-methoxycarbonylindol-3-yl)butyl]-4-(chroman-6-yl)piperazine;

of ethyl 3-(4-chlorobutyl)-5-indolecarboxylate with 1-(benzofuran-5-yl)piperazine:

1-[4-(5-ethoxycarbonylindol-3-yl)butyl]-4-(benzofuran-5-yl)piperazine;

of 3-(4-chlorobutyl)-5-methoxyindole with 1-(benzofuran-5-yl)piperazine:

1-[4-(5-methoxyindol-3-yl)butyl]-4-(benzofuran-5-yl)piperazine;

of 3-(4-chlorobutyl)-5-methoxycarbonylindole with 1-(chromen-4-on-6-yl)piperazine:

1-[4-(5-methoxycarbonylindol-3-yl)butyl]-4-(chromen-4-on-6-yl)piperazine;

of 3-(4-chlorobutyl)-5-cyanoindole with 1-(chromen-4-on-6-yl)piperazine:

1-[4-(5-cyanoindol-3-yl)butyl]-4-(chromen-4-on 6-yl)piperazine;

of 3-(4-chlorobutyl)-5-chloroindole with 1-(2,3-dihydrobenzofuran- 5-yl)piperazine:

1-[4-(5-chloroindol-3-yl)butyl]-4-(2,3-dihydrobenzofuran- 5-yl)piperazine;

of 3-(4-chlorobutyl)-5-methoxycarbonylindole with 1-(2,3-dihydrobenzofuran-5-yl)piperazine:

1-[4-(5-methoxycarbonylindol-3-yl)butyl]-4-(2,3-dihydrobenzofuran- 5-yl)piperazine;

of 3-(4-chlorobutyl)-5-methoxycarbonylindole with 4-(2,3-dihydrobenzofuran-5-yl)piperidine:

1-[4-(5-methoxycarbonylindol-3-yl)butyl]-4-(2,3-dihydrobenzofuran- 5-yl)piperidine;

of 3-(4-chlorobutyl)-5-methoxycarbonylindole with 4-(2,3-dihydrobenzofuran-5-yl)-4-hydroxypiperidine:

1-[4-(5-methoxycarbonylindol-3-yl)butyl]-4-(2,3-dihydrobenzofuran- 5-yl)-4-hydroxypiperidine;

of 3-(4-chlorobutyl)-5,6-dimethoxindole with 1-(chroman-6-yl)piperazine:

1-[4-(5,6-dimethoxyindol-3-yl)butyl]-4-(chroman-6-yl)piperazine;

of 3-(4-chlorobutyl)-5-cyanoindole with 1-(2-carboxybenzofuran- 5-yl)piperazine:

1-[4-(5-cyanoindol-3-yl)butyl]-4-(2-carboxybenzofuran-5-yl)piperazine;

of 3-(4-chlorobutyl)-6-fluoroindole with 1-(2,3-dihydrobenzofuran- 5-yl)piperazine:

1-[4-(6-fluoroindol-3-yl)butyl]-4-(2,3-dihydrobenzofuran- 5-yl)piperazine.

Example 2

1.8 g of 1-[4-(5-methoxycarbonylindol-3-yl)-butyl]-4-(chroman-6-yl)piperazine [obtainable according to Example 1] are boiled for 0.5 hours with 100 ml of 2N ethanolic KOH, worked up in the customary manner and give 1-[4-(5-carboxyindol-3-yl)butyl]-4-(chreman-6-yl)piperazine.

The following are obtained analogously by alkaline hydrolysis of the corresponding esters starting from 1-[4-(5-ethoxycarbonylindol-3-yl)butyl]-4-(benzofuran-5-yl)piperazine:

1-[4-(5-carboxyindol-3-yl)butyl]-4-(benzofuran-5-yl)piperazine:

from 1-[4-(5-methoxycarbonylindol-3-yl)butyl]-4-(chromen-4-on-6-yl)piperazine:

1-[4-(5-carboxyindol-3-yl)butyl]-4-(chromen-4-on-6-yl)piperazine;

from 1-[4-(5-methoxycarbonylindol-3-yl)butyl]-4-(2,3-dihydrobenzofuran- 5-yl)piperazine:

1-[4-(5-carboxyindol-3-yl)butyl]-4-(2,3-dihydrobenzofuran- 5-yl)piperazine;

from 1-[4-(5-methoxycarbonylindol-3-yl)butyl]-4-(2,3-dihydrobenzofuran- 5-yl)-4-hydroxypiperidine;

1-[4-(5-carboxyindol-3-yl)butyl]-4-(2,3-dihydrobenzofuran- 5-yl)-4-hydroxypiperidine.

Example 3

2.8 g of 1-[4-(5-carboxyindol-3-yl)butyl]-4-(2,3-dihydrobenzofuran-5-yl)piperazine are suspended in 100 ml of N-methylpyrrolidine. 3.2 g of 2-chloro-1-methylpyridinium methanesulfonate are then added and the mixture is stirred at room temperature for 12 hours. Dried NH$_3$ gas is then passed into the resulting solution until it is saturated and the mixture is stirred again for 10 hours. Customary working up gives 1-[4-(5-carbamoylindol-3-yl)butyl]-4-(2,3-dihydrobenzofuran-5-yl)-piperazine.

The following are obtained analogously by amidation of the following carboxylic acids with 2-chloro-1-methylpyridinium methanesulfonate:

from 1-[4-(5-carboxyindol-3-yl)butyl]-4-(2,3-dihydrobinzofuran- 5-yl)piperidine

1-[4-(5-carbamoylindol-3-yl)butyl]-4-(2,3-dihydrobenzofuran- 5-yl)piperidine, m.p. 155–157°;

from 1-[4-(5-carboxyindol-3-yl)butyl]-4-(2,3-dihydrobenzofuran- 5-yl)-4-hydroxypiperidine 1-[4-(5-carbamoylindol-3-yl)butyl]-4-(2,3-dihydrobenzofuran- 5-yl)-4-hydroxypiperidine, m.p. 69° (dec.);

from 1-[4-(5-carboxyindol-3-yl)butyl]-4-(chroman-6-yl)piperazine

1-[4-(5-carbamoylindol-3-yl)butyl]-4-(chroman-6-yl)piperazine.

Example 4

Analogously to Example 3, starting from 1-[4-(5-cyanoindol-3-yl)butyl]-4-(2-carboxybenzofuran-5-yl)piperazine reaction with 2-chloro-1-methylpyridinium methanesulfonate gives 1-[4-(5-cyanoindol-3-yl)butyl]-4-(2-carbamoylbenzofuran-5-yl)piperazine, m.p. 269–272° (hydrochloride).

Example 5

A mixture of 2.6 g of 3-(2-aminoethyl)-5-cyanoindole [obtainable by reaction of 5-cyanoindole with 2-chloroacetyl chloride to give 3-(2-chloroacetyl)-5-cyanoindole, subsequent reduction with diborane, reaction with phthalimide and hydrolysis] and one equivalent of 5-[N,N-bis(2-chloroethyl)amino]benzofuran [obtainable by reaction of 2-chloroacetyl chloride with 5-aminobenzofuran and subsequent reduction with diborane] in 40 ml of acetone and 40 ml of water is boiled for 20 hours and then worked up in the customary manner. 1-[2-(5-Cyanoindol-3-yl)ethyl]-4-(benzofuran-5-yl)piperazine is obtained.

The following are obtained analogously by reaction of 5-[N,N-bis(2-chloroethyl)amino]benzofuran with 3-(4-aminobutyl)-5-methoxymethylindole:

1-[4-(5-methoxymethylindol-3-yl)butyl]-4-(benzofuran-5-yl)piperazine; with 3-(3-aminopropyl) -5-hydroxyindole:

1-[3-(5-hydroxyindol-3-yl)propyl ]-4-(benzofuran-5-yl)piperazine;

with 3-(2-aminoethyl)-5-methoxyindole:

1-[2-(5-methoxyindol-3-yl)ethyl ]-4-(benzofuran-5-yl)piperazine;

with methyl 3-(3-aminopropyl)-5-indolecarboxylate:

1-[3-(5-methoxycarbonylindol-3-yl)propyl]-4-(benzofuran- 5-yl)piperazine;

with ethyl 3-(2-aminoethyl)-5-indolecarboxylate:

1-[2-(5-ethoxycarbonylindol-3-yl)ethyl]-4-(benzofuran-5-yl)piperazine;

with 3-(4-aminobutyl)-5-fluoroindole:

1-[4-(5-fluoroindol-3-yl)butyl]-4-(benzofuran-5-yl)piperazine;

with 3-(3-aminopropyl)-5-cyanoindole:

1-[3-(5-cyanoindol-3-yl)propyl]-4-(benzofuran- 5-yl)piperazine.

Example 6

Analogously to Example 5, reaction of 3.2 g of 3-(2-aminoethyl)-5-methoxyindole with 1.3 equivalents of 6-[N,N-bis(2-chloroethyl)amino]chroman [obtainable by reaction of 2-chloroacetyl chloride with 6-aminochroman and subsequent reduction with diborane] gives 1-[2-(5-methoxyindol-3-yl)ethyl]-4-(chroman-6-yl)piperazine.

The following are obtained analogously by reaction of 6-[N,N-bis(2-chloroethyl)amino]chroman with 3-(4-aminobutyl)-5-methoxymethylindole:

1-[4-(5-methoxymethylindol-3-yl)butyl]-4-(chroman-6-yl)piperazine;

with 3-(3-aminopropyl)-5-hydroxyindole:

1-[3-(5-hydroxyindol-3-yl)propyl]-4-(chroman-6-yl)-piperazine;

with 3-(2-aminoethyl)-5-methoxyindole:

1-[2-(5-methoxyindol-3-yl)ethyl]-4-(chroman-6-yl)piperazine;

with methyl 3-(3-aminopropyl)-5-indolecarboxylate:

1-[3-(5-methoxycarbonylindol-3-yl)propyl]-4-(chroman-6-yl)piperazine;

with ethyl 3-(2-aminoethyl)-5-indolecarboxylate:

1-[2-(5-ethoxycarbonylindol-3-yl)ethyl]-4-(chroman-6-yl)piperazine;

with 3-(4-aminobutyl)-5-fluoroindole:

1-[4-(5-fluoroindol-3-yl)butyl]-4-(chroman-6-yl)-piperazine;

with 3-(3-aminopropyl ) -5-cyanoindole:

1-[3-(5-cyanoindol-3-yl) propyl ]-4-(chroman-6-yl )piperazine.

Example 7

A solution of 3.9 g of 1-[4-(5-carboxyindol-3-yl)butyl]-4-(2,3-dihydrobenzofuran-5-yl)piperazine in 250 ml of DMF is treated with 1 g of N-methylmorpholine. A solution of one equivalent of tert-butylamine in 5 ml of DMF, 1.3 g of 1-hydroxybenzotriazole and a solution of 1.9 g of N-(3-dimethylaminopropyl)-N'-ethylcarbodiimide hydrochloride in 20 ml of DMF are added with stirring. The mixture is stirred at room temperature for 16 hours and the filtrate is evaporated. Customary working up gives 1-[4-(5-N-tert-butylcarbamoylindol-3-yl)butyl]-4-(2,3-dihydrobenzofuran-5-yl)piperazine.

The following are obtained analogously by reaction with tert-butylamine starting from 1-[4-(5-carboxyindol-3-yl)butyl]-4-(chroman-6-yl)piperazine:

1-[4-(5-N-tert-butylcarbamoylindol-3-yl)butyl]-4-(chroman-6-yl)piperazine;

from 1-[4-(5-cyanoindol-3-yl)butyl]-4-(2-carboxybenzofuran- 5-yl)piperazine:

1-[4-(5-cyanoindol-3-yl)butyl]-4-(2-N-tert-butyl-carbamoylbenzofuran- 5-yl)piperazine.

Example 8

A mixture of 2.1 g of 1-[4-(5-methoxyindol-3-yl)butyl]-4-(chroman-6-yl)piperazine [can be prepared according to Example 1], 1.8 g of pyridine hydrochloride and 50 ml of pyridine is boiled for 3 hours. It is cooled and evaporated, and the residue is worked up in the customary manner and gives 1-[4-(5-hydroxyindol-3-yl)-butyl]-4-(chroman-6-yl)piperazine, m.p. 220°–222°.

The following are obtained analogously from 1-[4-(5-methoxyindol-3-yl)butyl]-4-(2,3-dihydrobenzofuran- 5-yl)piperazine:

1-[4-(5-hydroxyindol-3-yl)butyl]-4-(2,3-dihydrobenzofuran- 5-yl)piperazine;

from 1-[4-(5-methoxyindol-3-yl)butyl]-4-(benzofuran-5-yl)piperazine:

1-[4-(5-hydroxyindol-3-yl)butyl]-4-(benzofuran-5-yl)piperazine;

from 1-[4-(5-methoxycarbonylindol-3-yl)butyl]-4-(chromen-4-on-6-yl)piperazine:

1-[4-(5-hydroxycarbonylindol-3-yl) butyl ]-4-(chromen-4-on-6-yl) piperazine;

from 1-[4-(5-methoxymethylindol-3-yl)butyl]-4-(benzofuran- 5-yl)piperazine:

1-[4-(5-hydroxymethylindol-3-yl)butyl]-4-(benzofuran-5-yl)piperazine;

from 1-[2-(5-methoxyindol-3-yl)ethyl]-4-(benzofuran-5-yl)piperazine:

1-[2-(5-hydroxyindol-3-yl)ethyl]-4-(benzofuran-5-yl)piperazine;

from 1-[2-(5-methoxyindol-3-yl)ethyl]-4-(benzofuran-5-yl)piperazine:

1-[2-(5-hydroxyindol-3-yl)ethyl]-4-(benzofuran-5-yl)piperazine.

Example 9

Analogously to Example 1, starting from 3-(4-chlorobutyl)-5-cyanoindole [obtainable by reaction of 5-cyanoindole with 4-chlorobutyryl chloride to give 3-(4-chlorobutyryl)-5-methoxyindole and subsequent reduction with $NaAlH_2(OCH_2CH_2OCH_3)_2$] by reaction with 1-(2-ethoxy-carbonylbenzofuran-5-yl)piperazine [obtainable by reaction of N,N-bis(2-chloroethyl)amine with 2-ethoxy-carbonyl-5-aminobenzofuran] gives, after customary working up, 1-[4-(5-cyanoindol-3-yl)butyl]-4-(2-ethoxy-carbonylbenzofuran- 5-yl)piperazine, m.p. 221°–223° (dihydrochloride).

The following are obtained analogously by reaction
of 3-(4-chlorobutyl)-5-methoxyindole with 1-(2-cyano-benzofuran- 5-yl)piperazine:

1-[4-(5-methoxyindol-3-yl)butyl]-4-(2-cyanobenzofuran-5-yl)piperazine;

of 3-(4-chlorobutyl)-5,6-dimethoxyindole with 1-(chroman-6-yl ) piperazine:

1-[4-(5,6-dimethoxyindol-3-yl)butyl ]-4-(chroman-6-yl)piperazine;

of 3-(4-chlorobutyl)-5,6-difluoroindole with 1-(chroman-6-yl)piperazine:

1-[4-(5,6-difluoroindol-3-yl)butyl]-4-(chroman-6-yl)piperazine;

of methyl 3-(4-chlorobutyl)-6-indolecarboxylate with 1-(chroman-6-yl)piperazine:

1-[4-(6-methoycarbonylindol-3-yl)butyl]-4-(chroman-6-yl)piperazine;

of ethyl 3-(3-chloropropyl)-6-indolecarboxylate with 1-(2-cyanobenzofuran-5-yl)piperazine:

1-[3-(6-ethoxycarbonylindol-3-yl)propyl]-4-(2-cyanobenzofuran- 5-yl)piperazine;

of 3-(4-chlorobutyl)-5-methoxyindole with 1-(2-N-methylcarbamoylbenzofuran- 5-yl)piperazine:

1-[4-(5-methoxyindol-3-yl)butyl]-4-(2-N-methylcarbamoylbenzofuran- 5-yl)piperazine;

of 3-(4-chlorobutyl)-6-chloroindole with 1-(chromen-4-on-6-yl)piperazine:

1-[4-(6-chloroindol-3-yl)butyl]-4-(chromen-4-on-6-yl)piperazine;

of 3-(2-chloroethyl)-5-cyanoindole with 1-(chromen-4-on-6-yl)piperazine:

1-[2-(5-cyanoindol-3-yl)ethyl]-4-(chromen-4-on-6-yl)piperazine;

of 3-(2-chloroethyl)-5,6-dichloroindole with 1-(2,3-dihydrobenzofuran- 5-yl)piperazine:

1-[2-(5,6-dichloroindol-3-yl)ethyl]-4-(2,3-dihydrobenzofuran- 5-yl)piperazine;

of 3-(4-chlorobutyl)-5-methoxycarbonylindole with 1-(2-carboxybenzofuran-5-yl)piperazine:

1-[4-(5-methoxycarbonylindol-3-yl)butyl]-4-(2-carboxybenzofuran- 5-yl)piperazine;

of 3-(2-chloroethyl)-5-methoxycarbonylindole with 4-(2-carboxybenzofuran-5-yl)piperidine:

1-[2-(5-methoxycarbonylindol-3-yl)ethyl]-4-(2-carboxybenzofuran- 5-yl)piperazine;

of 3-(4-chlorobutyl)-6-methoxycarbonylindole with 4-(3-carboxybenzofuran-5-yl)-4-hydroxypiperidine:

1-(4-(6-methoxycarbonylindol-3-yl)butyl]-4-(3-carboxybenzofuran- 5-yl)-4-hydroxypiperidine;

of 3-(4-chlorobutyl)-7-methoxycarbonylindole with 4-(3-carboxybenzofuran-5-yl)-4-hydroxypiperidine;

1-[4-(7-methoxycarbonylindol-3-yl)butyl]-4-(3-carboxybenzofuran- 5-yl)-4-hydroxypiperidine;

of 3-(4-chlorobutyl)-5,6-dimethoxyindole with 1-(2-carboxybenzofuran- 5-yl)piperazine:

1-[4-(5,6-dimethoxyindol-3-yl)butyl]-4-(2-carboxybenzofuran- 5-yl)piperazine.

Example 10

A solution of 3.6 g of 1-[4-(5-methoxycarbonylindol-3-yl)butyl]-4-(chromen-4-on-6-yl)piperazine in 40 ml of THF is added dropwise with stirring at room temperature to a suspension of 0.6 g of lithium aluminum hyride in 20 ml of THF. The mixture is then stirred for a further hour at 25° C., 20 ml of dilute sodium hydroxide solution are added, the mixture is filtered and the filtrate is worked up in the customary manner. 1-[4-(5-Hydroxymethylindol-3-yl)butyl]-4-(chromen-4-on-6-yl)piperazine is obtained.

The following are obtained analagously by reduction
of 1-[4-(5-methoxycarbonylindol-3-yl)butyl]-4-(chroman-6-yl)piperazine 1-[4-(5-hydroxymethylindol-3-yl)butyl]-4-(chroman-6-yl)piperazine;

of 1-[4-(5-methoxycarbonylindol-3-yl)butyl]-4-benzofuran-5yl)piperazine

1-[4-(5-hydroxymethylindol-3-yl)butyl]-4-(benzofuran-5-yl)piperazine;

of 1-[3-(5-methoxycarbonylindol-3-yl)propyl]-4-(chroman-6-yl) piperidine

1-[3-(5-hydroxymethylindol-3-yl)propyl]-4-(chroman-6-yl)piperidine of 1-[2-(5-methoxycarbonylindol-3-yl)ethyl]-4-chroman-6-yl) piperidine 1-[2-(5-hydroxymethylindol-3-yl)ethyl]-4-(chroman-6-yl)piperidine.

Example 11

HCl gas is passed into a boiling solution of 2.5 g of 1-[4-(5-carboxyindol-3-yl)butyl]-4-(2,3-dihydrobenzofuran- 5-yl)piperazine in 50 ml of absolute methanol for 2 hours. The mixture is then boiled for a further hour, worked up in the customary manner and gives 1-[4-(5-methoxycarbonylindol-3-yl)butyl]-4-(2,3-dihydrobenzofuran- 5-yl)piperazine.

The following are obtained analagously by esterification of 1-[4-(5-carboxyindol-3-yl)butyl]-4-(2,3-dihydrobenzofuran-5-yl)-4-hydroxypiperidine:

1-[4-(5-methoxycarbonylindol-3-yl)butyl]-4-(2,3-dihydrobenzofuran-5-yl)-4-hydroxypiperidine;

of 1-[4-(5-carboxyindol-3-yl)butyl]-4-(chroman-6-yl)-piperazine:

1-[4-(5-methoxycarbonylindol-3-yl)butyl]-4-(chroman-6-yl)piperazine;

of 1-[4-(5-cyanoindol-3-yl)butyl]-4-(2-carboxybenzofuran-5-yl)piperazine:

1-[4-(5-cyanoindol-3-yl)butyl]-4-(2-methoxycarbonylbenzofuran-5-yl)piperazine.

Example A

Injection vials

A solution of 100 g of an active ingredient of the formula I and 5 g of disodium hydrogen phosphate in 3 l of double-distilled water is adjusted to pH 6.5 with 2N hydrochloric acid, sterile-filtered, filled into injection vials, lyophilized and sterile-sealed. Each injection vial contains 5 mg of active ingredient.

Example B

Suppositories

A mixture of 20 mg of an active ingredient of the formula I is melted with 100 g of soya lecithin and 1,400 g of cocoa butter, poured into moulds and allowed to cool. Each suppository contains 20 mg of active ingredient.

Example C

Solution

A solution of 1 g of an active ingredient of the formula I, 9.38 g of $NaH_2PO_4 \times 2H_2O$, 28.48 g $Na_2HPO_4 \times 12 H_2O$ and 0.1 g of benzalkonium chloride is prepared in 940 ml of double-distilled water. The pH is adjusted to 6.8, and the solution is made up to 1 l and sterilized by irradiation. This solution can be used in the form of eyedrops.

Example D

Ointment 500 mg of an active ingredient of the formula I are mixed with 99.5 g of petroleum jelly under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is compressed to tablets in conventional manner so that each tablet contains 10 mg of active ingredient.

Example F

Coated tablets

Tablets are formed by compression analogously to Example E and then covered in conventional manner with a coating of sucrose, potato starch, talc, tragacanth and colorant.

Example G

Capsules 2 kg of active ingredient of the formula I are filled into hard gelatin capsules in conventional manner so that each capsule contains 20 mg of the active ingredient.

Example H

Ampoules

A solution of 1 kg of active ingredient of the formula I in 60 l of double-distilled water is filled into ampoules and lyophilized under aseptic conditions and the ampoules are sealed under sterile conditions. Each ampoule contains 10 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound according to formula I

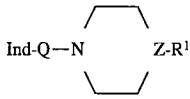

wherein

Ind is unsubstituted indol-3-yl, indol-3-yl monosubstituted by OH, OA, CN, Hal, $COR^2$ or $CH_2R^2$, or indol-3-yl polysubstituted by OH, OA, CN, Hal, $COR^2$, $CH_2R^2$ or combinations thereof;

$R^1$ is benzofuran-5-yl, chroman-4-on-6-yl, 3-chromen-6-yl or chromen-4-on-6-yl, which in each case is unsubstituted or monosubstituted by CN, $CH_2OH$, $CH_2OA$ or $COR^2$;

Q is $C_mH_{2m}$;

Z is N;

A is alkyl having 1–6 C atoms;

Hal is F, Cl, Br or I;

$R^2$ is OH, OA, $NH_2$, NHA or $NA_2$;

$R^3$ is H, OH or OA; and m is 2, 3 or 4; or a physiologically acceptable salt thereof.

2. A compound according to claim 1, wherein said compound is:

(a) 1-[4-(5-methoxyindol-3-yl)butyl]-4-(2-hydroxymethylbenzofuran-5-yl)piperazine or a physiologically acceptable salt thereof;

(b) 1-[4-(5-cyanoindol-3-yl)butyl]-4-(2-ethoxycarbonylbenzofuran-5-yl ) piperazine or a physiologically acceptable salt thereof; or (c) 1-[4-(5-cyanoindol-3-yl)butyl]-4-(2-carbamoylbenzofuran-5-yl) piperazine or a physiologically acceptable salt thereof.

3. A compound according to claim 1, wherein Ind is unsubstituted indol-3-yl, indol-3-yl monosubstituted by OH, OA, CN, Hal, $COR^2$ or $CH_2R^2$, or indol-3-yl disubstituted by OH, OA, CN, Hal, $COR^2$ or $CH_2R^2$.

4. A compound according to claim 1, wherein Ind is indol-3-yl monosubstituted in the 5-position by OH, OA, CN, Hal, $COR^2$ or $CH_2R^2$.

5. A compound according to claim 1, wherein Ind is indol-3-yl monosubstituted in the 4-, 6- or 7-position by OH, OA, CN, Hal, $COR^2$ or $CH_2R^2$.

6. A compound according to claim 1, wherein A is methyl or ethyl.

7. A compound according to claim 1, wherein $R^1$ is benzofuran-5-yl, or chroman-4-on-6-yl which, in each case is unsubstituted or monosubstituted by —$CH_2OH$, —$CONH_2$, —$CO_2A$ or —$CO_2NHA$.

8. A compound according to claim 1, wherein Q is —$(CH_2)_4$—.

9. A compound according to claim 1, wherein Ind is indol-3-yl substituted in the 5-position by OH or OA.

10. A compound according to claim 1, wherein Ind is indol-3-yl substituted in the 5-position by $CONH_2$ or CN.

11. A compound according to claim 1, wherein $R^1$ is unsubstituted benzofuran-5-yl or benzofuran-5-yl substituted by CN, $CH_2OH$, $CH_2OA$ or $COR^2$.

12. A compound according to claim 1, wherein $R^1$ is chromen-4-on-6-yl.

13. A compound according to claim 1, wherein $R^1$ is unsubstituted 3-chromen-6-yl or 3-chromen-6-yl substituted by CN, $CH_2OH$, $CH_2OA$ or $COR^2$.

14. A compound according to claim 1, wherein $R^1$ is unsubstituted chroman-4-on-6-yl or chroman-4-on-6-yl substituted by CN, $CH_2OH$, $CH_2OA$ or $COR^2$.

15. A compound according to claim 1, wherein $R^1$ is unsubstituted chromen-4-on-6-yl or chromen-4-on-6-yl substituted by CN, $CH_2OH$, $CH_2OA$ or $COR^2$.

16. A pharmaceutical composition comprising a compound according to claim 1 and a pharmaceutically acceptable carrier.

17. A composition according to claim 16, wherein said compound is present in an amount of 0.2–500 mg.

* * * * *

UNITED STATES PATENT AND TRADEMARK OFFICE
CERTIFICATE OF CORRECTION

PATENT NO. : 5,532,241 Page 1 of 1
APPLICATION NO. : 08/314734
DATED : July 2, 1996
INVENTOR(S) : Henning Bottcher et al.

It is certified that error appears in the above-identified patent and that said Letters Patent is hereby corrected as shown below:

Column 16, Line 46, please delete "$R^3$ is H, OH or OA;"

Signed and Sealed this

Tenth Day of November, 2009

David J. Kappos
*Director of the United States Patent and Trademark Office*